(12) United States Patent
Greenberg et al.

(10) Patent No.: US 8,380,326 B2
(45) Date of Patent: Feb. 19, 2013

(54) INSULATED IMPLANTABLE ELECTRICAL CIRCUIT

(75) Inventors: Robert Greenberg, Los Angeles, CA (US); Neil Hamilton Talbot, Montrose, CA (US); Jerry Ok, Canyon Country, CA (US); Jordan Matthew Neysmith, Pasadena, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 1820 days.

(21) Appl. No.: 10/638,989

(22) Filed: Aug. 11, 2003

(65) Prior Publication Data

US 2007/0158100 A1 Jul. 12, 2007

Related U.S. Application Data

(60) Provisional application No. 60/402,591, filed on Aug. 9, 2002.

(51) Int. Cl.
*A61N 1/04* (2006.01)
(52) U.S. Cl. ........................................................ 607/152
(58) Field of Classification Search .................... 607/152
See application file for complete search history.

(56) References Cited

U.S. PATENT DOCUMENTS

| 3,699,970 | A | | 10/1972 | Brindley et al. |
| 3,977,392 | A | * | 8/1976 | Manley ........................ 600/392 |
| 4,573,481 | A | | 3/1986 | Bullara et al. |
| 4,837,049 | A | | 6/1989 | Byers et al. |
| 5,067,491 | A | * | 11/1991 | Taylor et al. .................. 600/561 |
| 5,109,844 | A | | 5/1992 | De Juan, Jr. et al. |
| 5,215,088 | A | | 6/1993 | Normann et al. |
| 5,476,496 | A | * | 12/1995 | Strandberg et al. ........... 607/122 |
| 5,935,155 | A | | 8/1999 | Humayun et al. |
| 6,374,143 | B1 | | 4/2002 | Berrang et al. |
| 6,400,989 | B1 | | 6/2002 | Eckmiller |
| 6,458,157 | B1 | | 10/2002 | Suaning |
| 2002/0187260 | A1 | * | 12/2002 | Sheppard et al. ........... 427/248.1 |
| 2003/0097165 | A1 | * | 5/2003 | Krulevitch et al. ........... 607/115 |
| 2003/0109903 | A1 | * | 6/2003 | Berrang et al. ................. 607/36 |
| 2004/0147825 | A1 | * | 7/2004 | Milojevic et al. ............. 600/372 |

OTHER PUBLICATIONS

M. Sonn and W.M. Feist; "A Prototype Flexible Microelectrode Array for Implant-Prosthesis Applications," *Medical and Biological Engineering*, 778-791, Nov. 1974.
T. Stieglitz, H. Beutel, M. Schuettler, and J.-U. Meyer, "Micromachined, Polyimide-Based Devices for Flexible Neural Interfaces," *Biomedical Microdevices*, 2:4, 283-294, 2000.
B. Ganesh, "*A Polyimide Ribbon Cable for Neural Recording and Stimulation Systems*," Thesis, University of Utah, Mar. 1998.
A. Schneider, T. Stieglitz, W. Haberer, H. Beutel, and J.-Uwe Meyer, "*Flexible Interconnects for Biomedical Microsystems Assembly*", IMAPS Conference, Jan. 31, 2001.

* cited by examiner

*Primary Examiner* — Joseph Dietrich
(74) *Attorney, Agent, or Firm* — Scott B. Dunbar; Gary Schnittgrund

(57) ABSTRACT

The invention is directed to an implant able insulated electrical circuit that utilizes polyparaxylylene, preferably as Parylene, a known polymer that has excellent living tissue implant characteristics, to provide for chronic implantation of conductive electrical devices, such as stimulators and sensors. The device is thin, flexible, electrically insulated, and stable after long exposure to living tissue. Layers of Parylene may be combined with layers of a polymer, such as polyimide, to yield greater design flexibility in the circuit. Multiple electrical conduction layers may be stacked in the circuit to increase packing density.

16 Claims, 1 Drawing Sheet

INSULATED IMPLANTABLE ELECTRICAL CIRCUIT

PRIORITY CLAIM

This application claims the benefit of U.S. Application No. 60/402,591 filed on Aug. 9, 2002.

FEDERALLY SPONSORED RESEARCH

This invention was made with government support under grant No. R24EY12893-01, awarded by the National Institutes of Health. The government has certain rights in the invention.

FIELD OF THE INVENTION

This invention relates to implant able medical devices, especially implant able cables and electrode arrays for stimulation, recording and interconnection.

BACKGROUND OF THE INVENTION

Arrays of electrodes for neural stimulation are commonly used for a variety of purposes. Some examples include U.S. Pat. No. 3,699,970 to Brindley, which describes an array of cortical electrodes for visual stimulation. Each electrode is attached to a separate inductive coil for signal and power. U.S. Pat. No. 4,573,481 to Bullara describes a helical electrode to be wrapped around an individual nerve fiber. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. U.S. Pat. No. 5,109,844 to de Juan describes a flat electrode array placed against the retina for visual stimulation. U.S. Pat. No. 5,935,155 to Humayun describes a retinal prosthesis for use with a flat retinal array.

Packaging of a biomedical device intended for implantation in the eye, and more specifically for physical contact with the retina, presents a unique interconnection challenge. The consistency of the retina is comparable to that of wet tissue paper and the biological media inside the eye is a corrosive saline liquid environment.

Thus, the device to be placed against the retina, in addition to being comprised of biocompatible, electrochemically stable materials, must appropriately conform to the curvature of the eye, being sufficiently flexible and gentle in contact with the retina to avoid tissue damage, as discussed by Schneider, et al. [see A. Schneider, T. Stieglitz, W. Haberer, H. Beutel, and J. Uwe Meyer, "Flexible Interconnects for Biomedical Microsystems Assembly," IMAPS Conference, Jan. 31, 2001.] It is also desirable that this device, an electrode array, provides a maximum density of stimulation electrodes. A commonly accepted design for an electrode array is a very thin, flexible circuit cable. It is possible to fabricate a suitable electrode array using discrete wires, but with this approach, a high number of stimulation electrodes cannot be achieved without sacrificing cable flexibility (to a maximum of about 16 electrodes).

Known insulators for implanted electrical circuits include polyimide and silicone dielectrics. They have limited lives once implanted. The polyimide slowly degrades upon exposure to the living tissue and allows water to reach the electrical conductor, eventually leading to at least partial electric current leakage.

Known techniques for implanted electrical circuits do not result in a hermetic package that is suitable for chronic implantation in living tissue. Therefore, it is desired to have an insulated electrical conductor that ensures that the electronic package will function for long-term implant applications in living tissue.

DETAILED DESCRIPTION OF THE PREFERRED EMBODIMENT

Figure 1:
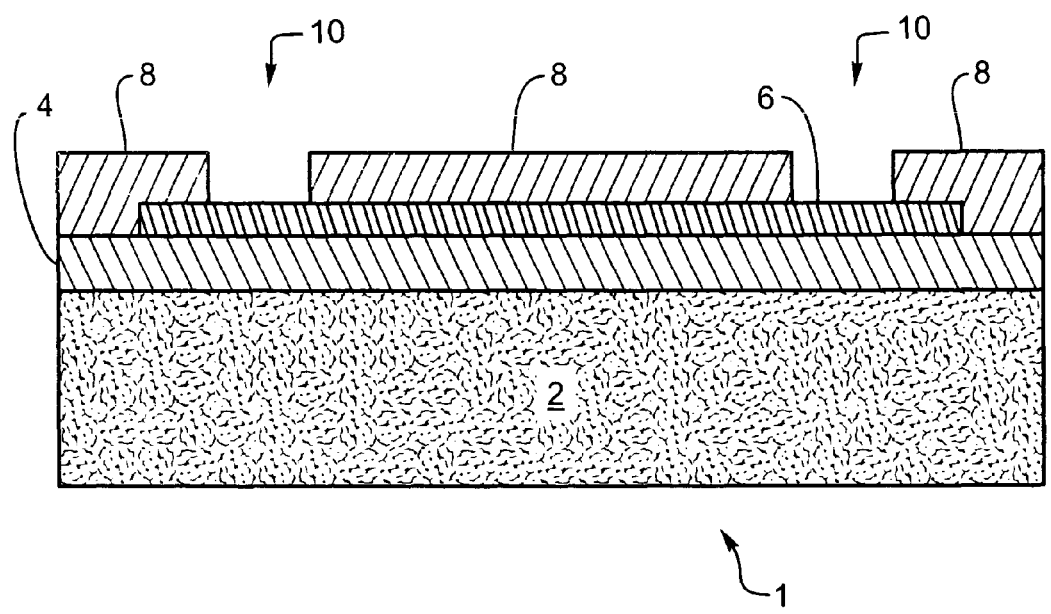
FIG. 1 illustrates a cross-sectional view of an implantable electrical circuit.

The preferred embodiment is an implantable insulated electrical circuit for electrical transmission within living organisms. These assemblies provide electrical conduction, isolation of the electrical conductors from the environment in the living tissue and from each other, and mechanical support for the electrical conductor. Electrical device assemblies that are commonly used for stimulation and or recording within the body benefit from the invention. Neural stimulators or sensors are of particular interest, including retinal electrode arrays. The implantable insulated electrical conductors may also be used to connect discrete components of an implanted medical device, permitting the transmission of electrical signals, power, as well as providing mechanical connection. Key attributes include good electrical insulation properties, low moisture absorption, appropriate mechanical characteristics and ease of fabrication.

Polyparaxylylene is a known polymer that has excellent implant characteristics. One example, Parylene, manufactured by Specialty Coating Systems (SCS), a division of Cookson Electronic Equipment Group, located in Indianapolis, Ind., is a preferred material. Parylene is available in various forms, such as Parylene C, Parylene D, and Parylene N, each having different properties. The preferred form is Parylene C, although it is recognized that many forms of polyparaxylylene may exist or may be developed that are suitable for this application.

The use of Parylene was mentioned, but not pursued, by Sonn and Feist. [see M. Sonn and W. M. Feist, "A Prototype Flexible Microelectrode Array for Implant-Prosthesis Applications," *Medical and Biological Engineering*, 778-791, November 1974.] Stieglitz, et al. published fabrication details of similar items manufactured using polyimide. [see T. Stieglitz, H. Beutel, M. Schuettler, and J. U. Meyer, "Micromachined, Polyimide-Based Devices for Flexible Neural Interfaces," *Biomedical Microdevices*, 2:4, 283-294, 2000.] Ganesh wrote a thesis on ribbon cables for neural recording and stimulation using polyimide [see B. Ganesh, "A Polyimide Ribbon Cable for Neural Recording and Stimulation Systems," Thesis, University of Utah, March 1998.] Parylene is widely used as an electrical insulating and barrier material in commercial electronic devices. It is well known to use Parylene as a conformal coating on printed circuit boards. While discrete wires have been coated with Parylene for implantation, such as with cochlear implants, the application of Parylene as an electrical insulator for implantable electrical circuits, as embodied by this invention, is unknown to the inventors.

The moisture vapor transmission rates compare favorably with those of other conformal coating materials. The rate for Parylene C is superior to almost all polymeric materials. The Parylenes resist room temperature chemical attack and are insoluble in organic solvents up to 150° C. Parylene C can be dissolved in chloro-napthalene at 175° C., and Parylene N is soluble at the solvent's boiling point (265° C.). The thermal properties are given in Table 1 and the electrical properties are given in Table 2.

TABLE 1

Parylene Thermal Properties (2)

| Properties | Method | Parylene N | Parylene C | Parylene D | Epoxides (1) | Silicones (1) | Urethanes (1) |
|---|---|---|---|---|---|---|---|
| Melting Point (° C.) | 1 | 420 | 290 | 380 | cured | cured | ~170 |
| T5 Point (° C.) (modulus = $10^5$ psi) | 1 | 160 | 125 | 125 | 110 | ~125 | ~30 |
| T4 Point (° C.) (modulus = $10^4$ psi) | 1 | >300 | 240 | 240 | 120 | ~80 | 0 |
| Linear Coefficient of Expansion at 25° C. ($\times 10^5$, (° C.)$^{-1}$) | — | 6.9 | 3.5 | 3-8 | 4.5-6.5 | 25-30 | 10-20 |
| Thermal Conductivity at 25° C. ($10^{-4}$ cal/(cm · s · ° C.)) | 2 | 3.0 | 2.0 | — | 4-5 | 3.5-7.5 | 5.0 |
| Specific Heat at 20° C. (cal/g ° C.) | — | 0.20 | 0.17 | — | 0.25 | — | 0.42 |

Test Methods 1. Taken from Secant modulus-temperature curve 2. ASTM C 177

(1) Properties and methods as reported in *Modern Plastics Encyclopedia*, issue for 1968, Vol. 45/No. 1A, McGraw Hill, New York, 1967

(2) After Specialty Coating Systems, Indianapolis, IN.

TABLE 2

Parylene Electrical Properties (3)

| Properties (1) | Parylene N | Parylene C | Parylene D | Epoxides (2) | Silicones (2) | Urethanes (2) |
|---|---|---|---|---|---|---|
| Dielectric Strength, dc volts/mil short time, 1 mil films[a] | 7,000 | 5,600 | 5.500 | | | |
| Corrected to ⅛ inch | 630 | 500 | 490 | 400-500 | 550 | 450-500 |
| Volume Resistivity ohm-cm, 23° C., 50% RH[b] | $1.4 \times 10^{17}$ | $8.8 \times 10^{16}$ | $1.2 \times 10^{17}$ | $10^{12}$-$10^{17}$ | $10^{15}$ | $10^{11}$-$10^{15}$ |
| Surface Resistivity, ohms, 23° C., 50% RH[b] | $10^{13}$ | $10^{14}$ | $10^{16}$ | $10^{13}$ | $10^{13}$ | $10^{14}$ |
| Dielectric Constant[c] | | | | | | |
| 60 Hz | 2.65 | 3.15 | 2.84 | 3.5-5.0 | 2.7-3.1 | 5.3-7.8 |
| 1 KHz | 2.65 | 3.10 | 2.82 | 3.5-4.5 | 2.6-2.7 | 5.4-7.6 |
| 1 MHz | 2.65 | 2.95 | 2.80 | 3.3-4.0 | 2.6-2.7 | 4.2-5.2 |
| Dissipation Factor | | | | | | |
| 60 Hz | 0.0002 | 0.020 | 0.004 | 0.002-0.01 | 0.001-0.007 | 0.015-0.05 |
| 1 KHz | 0.0002 | 0.019 | 0.003 | 0.002-0.02 | 0.001-0.005 | 0.04-0.06 |
| 1 MHz | 0.0006 | 0.013 | 0.002 | 0.03-0.05 | 0.001-0.002 | 0.05-0.07 |

[a] ASTM D 149

[b] ASTM D 257, 1 in$^2$ mercury electrodes

[c] ASTM D 150, 1 in$^2$ (1) Properties measured on Parylene films, 0.001 in thick.

(2) Properties and methods as reported in *Modern Plastics Encyclopedia*, issue for 1968, vol. 45, No. 1A, McGraw Hill, NY, 1967.

(3) After Specialty Coating Systems, Indianapolis, IN.

A cross-sectional view of a preferred embodiment of the invention is presented in FIG. 1. An electrical circuit 1 is shown generally being formed on a rigid substrate. The substrate 2 may be selected from glass or ceramic, such as alumina or silicon. Substrate 2 is preferably comprised of glass.

A first Parylene layer 4 is deposited on the substrate 2 from a vapor phase that is produced by known techniques, such as thermal decomposition. It is known that Parylene is the polymer "polyparaxylylene" and that any source of this material may be used to implement this invention. The inventors use the term Parylene, as is common in industry practice, to indicate the class of polyparaxylylene polymers.

A method of forming an insulated flexible electrical circuit 1 suitable for implantation, comprising the steps of: choosing a rigid substrate 2; cleaning said rigid substrate 2; depositing a first polyparaxylylene layer 4 on said rigid substrate 2; depositing an electrical conductor 6 on said first polyparaxylylene layer 4; patterning said electrical conductor 6 to form a conductive path thereon; depositing a second polyparaxylylene layer 8; defining at least one select portion of said second polyparaxylylene layer 8; and removing said at least one select portion of said second polyparaxylylene layer 8 defining at least one aperture 10 therein, thereby forming at least one electrode that is suitable for contacting living tissue.

An electrical conductor 6 is deposited by a known physical vapor deposition method, such as sputtering or evaporation. While the preferred embodiment is to an electrical conductor 6 that is comprised of one material, it is clear that the electrical conductor 6 may also be comprised of layers of several materials. Alternatively, the conductor 6 or combination thereof may be deposited by other known methods, such as direct write, plating, or electrophoresis. The electrical conductor 6 is patterned by known techniques, such as lift-off or etching. The electrical conductor 6 may be comprised of a single metal or in an alternate embodiment, from several metals that may be layered or alloyed, that are selected from a group of electrically conductive biocompatible materials having favorable electrochemical characteristics, such as titanium, platinum, gold, iridium, and their alloys. Multiple metals may be used in order to achieve desired characteristics. For example, adhesion and barrier layers are commonly used in electronics where individual metal layers are combined to yield a more functional circuit stack. These electrical conduction paths, traces, bond pads, and electrode sites are formed prior to depositing a second layer of Parylene 8 to the device. Typical thicknesses of each Parylene layer are in the range of 0.5 to 50 microns, and preferably are about 3 to 15 microns thick. An alternate embodiment uses metals that are not biocompatible, so long as they are completely encapsulated by the surrounding structural elements and thus do not contact living tissue.

In an alternate embodiment, non-biocompatible materials, such as chrome, silver, or copper may be used as the electrical conductor 6. The electrical conductor 6 is then coated with a biocompatible, hermetic coating in the exposed aperture 6 area. This coating is preferably titanium nitride, although in alternative embodiments it may be an electrically conductive biocompatible metal, such as titanium, platinum, gold, iridium, or their alloys. The Parylene layers cover and protect the rest of the electrical conductor 6.

Apertures 10 are patterned by known techniques, such as by dry etching or laser ablation, or by reactive ion etching. The apertures 10 permit electrical conduction to either tissue or a connected implanted device. The apertures 10 define an electrode area on the electrical conductor 6.

The rigid substrate 2 is removed by known techniques, such as mechanical separation or etching, where mechanical separation is the preferred technique.

As a further embodiment of the invention, adhesion between the first layer of Parylene 4 and the second layer of Parylene 8 is preferably improved by one or more of the following techniques:

(a) Silane application between Parylene layers.

(b) Chemical modification of the Parylene surface to create an energetic, a reactive, or an amorphous surface (Parylene is amorphous as deposited).

(c) Roughening of the Parylene surface.

(d) Thermal compression of the Parylene layers.

Techniques (b) and (c) can used to improve the metal to Parylene adhesion, if applied prior to metal deposition.

More than one electrical conductor 6 may be deposited adjacent to the Parylene. Additional metal layers may be deposited that are protected by additional Parylene layers, such that a multilayered higher density electrical circuit is achieved.

Figure 2:
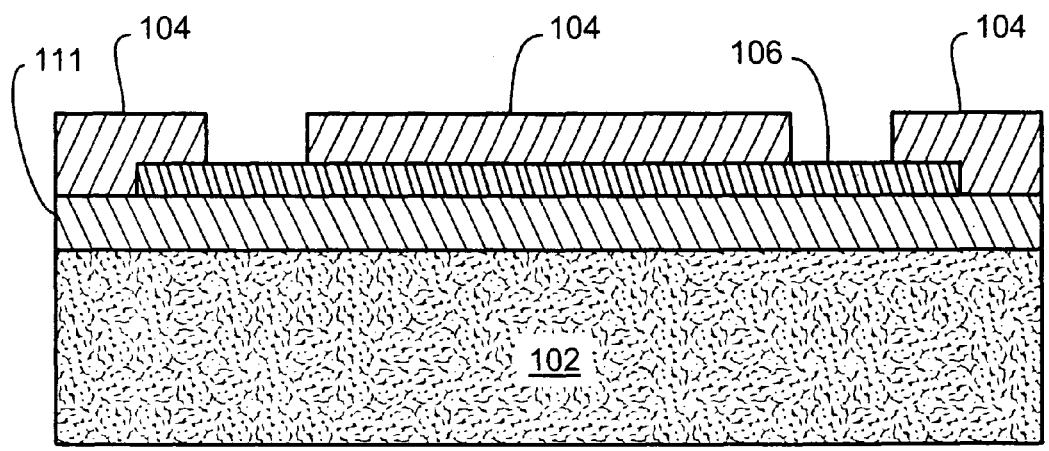
FIG. 2 illustrates a cross-sectional view of an alternate implantable electrical circuit.

A further alternative embodiment, FIG. 2, of the invention preferably replaces the first layer of Parylene 4 with a polymer layer 111, which is preferably polyimide, such that beginning with the rigid substrate 102, the layers are, preferably, polymer layer 111 (polyimide)—electrical conductor 106—layer of Parylene 104. The polyimide is preferably applied as a liquid.

In an alternative embodiment, not illustrated, one applies a first polymer coating, preferably polyimide, prior to depositing the first Parylene layer, such that beginning with the rigid substrate, the layers are, polymer layer (preferably polyimide)—first Parylene layer—electrical conductor—second layer of Parylene.

In yet another embodiment, not illustrated, a polymer coating, preferably of polyimide is applied between the Parylene layer and the electrical conductor.

In further embodiments, not illustrated, a polymer coating, preferably of polyimide is deposited on either side of the second layer of Parylene, either in the presence or absence of a polymer coating on the first layer of Parylene.

Obviously, many modifications and variations of the present invention are possible in light of the above teachings. It is therefore to be understood that, within the scope of the appended claims, the invention may be practiced otherwise than as specifically described.

What is claimed is:

1. A method of forming an insulated flexible electrical circuit suitable for implantation, comprising the steps of:
   choosing a rigid substrate;
   cleaning said rigid substrate;
   depositing a first polyparaxylylene layer on said rigid substrate;
   selecting a biocompatible metal or metal combination to comprise an electrical conductor;
   depositing said selected metal or metal combination forming an electrical conductor on said first polyparaxylylene layer;
   patterning said electrical conductor to form a conductive path thereon;
   depositing a second polyparaxylylene layer;
   thermally treating said first polyparaxylylene layer and said second polyparaxylylene layer;
   defining at least one select portion of said second polyparaxylylene layer;
   removing said at least one select portion of said second polyparaxylylene layer defining at least one aperture therein, thereby forming at least one electrode that is suitable for contacting living tissue; and removing said rigid substrate wherein said implantable insulated flexible electrical circuit comprising polyparaxylylene and metal structure results.

2. The method of claim 1, wherein said step of choosing a rigid substrate is accomplished by choosing said substrate comprised of glass.

3. The method of claim 1, further comprising the step of enhancing said first polyparaxylylene layer for adhesion after said step of depositing a first polyparaxylylene layer.

4. The method of claim 1, further comprising the step of enhancing said electrical conductor for adhesion after said step of patterning said electrical conductor to form a conductive path.

5. The method of claim 1, further comprising the step of enhancing said first polyparaxylylene layer for adhesion before said step of depositing a second polyparaxylylene layer.

6. The method of claim 1, further comprising the step of applying silane to enhance adhesion.

7. The method of claim 1, further comprising the step of modifying by chemical means said first polyparaxylylene layer.

8. The method of claim 1, further comprising the step of roughening the polyparaxylylene surface.

9. The method of claim 1, further comprising the step of compressing thermally said first polyparaxylylene layer and said second polyparaxylylene layer to increase adhesion.

10. The method of claim 1, wherein said step of removing said at least one select portion of said second polyparaxylylene layer is accomplished by etching with reactive ions.

11. The method of claim 1, wherein said step of selecting a metal or metal combination to comprise an electrical conductor is selecting a metal or metal combination selected from the group consisting of titanium, platinum, gold, iridium, and their alloys.

12. The method of claim 1, wherein said step of selecting a metal or metal combination to comprise an electrical conductor is selecting a layered metal combination where said layered metal combination is selected from the group consisting of titanium, platinum, gold, iridium, and their alloys.

13. The method of claim 1, wherein said step of selecting a metal or metal combination to comprise an electrical conductor is selecting a non-biocompatible metal or metal combination selected from the group consisting of chrome, silver, or copper, and their alloys.

14. The method of claim 13, further comprising the step of coating said non-biocompatible metal or metal combination with a hermetic coating.

15. The method of claim 13, further comprising the step of coating said non-biocompatible metal or metal combination with a biocompatible, hermetic coating comprised of titanium nitride.

16. The method of claim 13, further comprising the step of coating said non-biocompatible metal or metal combination with an electrically conductive, biocompatible, hermetic coating selected from the group consisting of titanium, platinum, gold, iridium, and their alloys.

* * * * *